Figure 1:
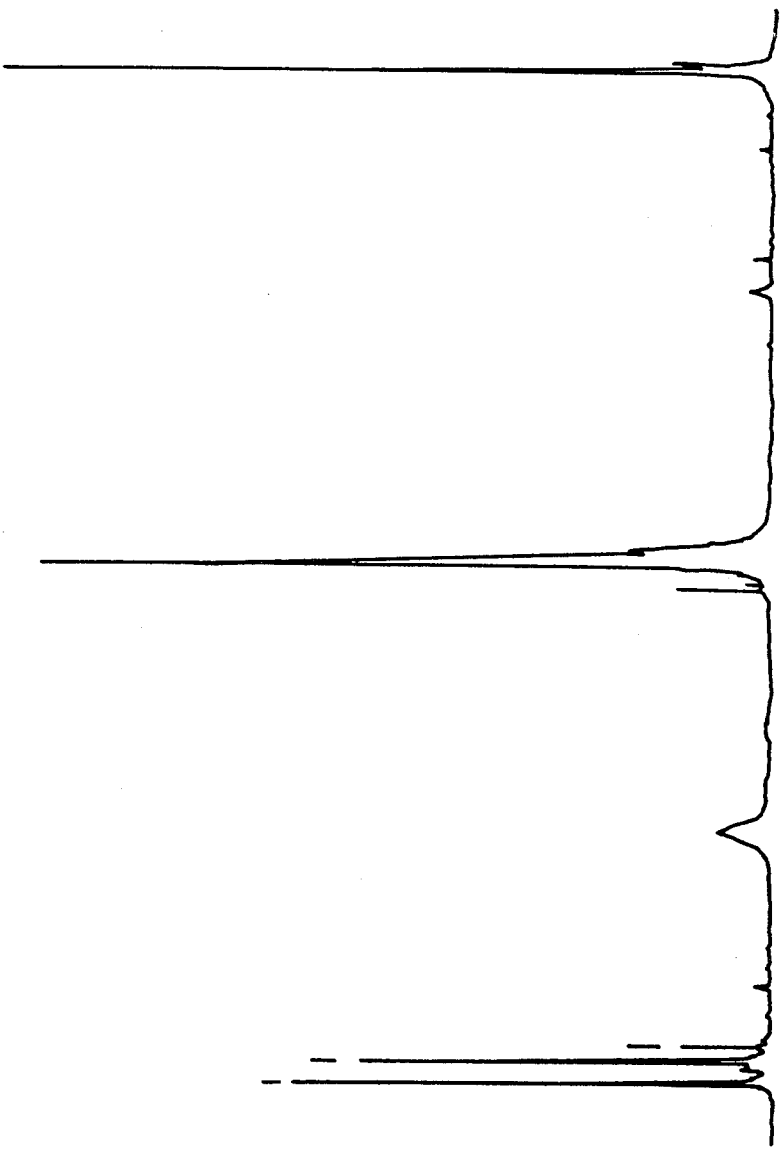

United States Patent [19]

Roger et al.

[11] Patent Number: 4,883,903

[45] Date of Patent: Nov. 28, 1989

[54] PROCEDURE FOR THE PREPARATION OF ACTIVATED NITROSOCARBAMATES

[75] Inventors: Pierre Roger, Montigny-les-Bretonneux; Jean-Paul Fournier; Rolande Leroy, both of Paris, all of France

[73] Assignee: Sanofi, Paris, France

[21] Appl. No.: 184,915

[22] Filed: Apr. 22, 1988

[30] Foreign Application Priority Data

Apr. 22, 1987 [FR] France .................................. 87 05708

[51] Int. Cl.$^4$ .................. C07C 125/067; C07C 69/96
[52] U.S. Cl. ..................................... 560/137; 558/282
[58] Field of Search ...................... 560/132, 137, 145; 564/33; 558/282

[56] References Cited

U.S. PATENT DOCUMENTS 3,345,256  10/1967  Haubein .............................. 560/137

FOREIGN PATENT DOCUMENTS 1020971  12/1957  Fed. Rep. of Germany .
1165494   9/1960  France .
2089433   1/1972  France .
2487343   1/1982  France .

OTHER PUBLICATIONS

Madelmont et al., Journal of Labelled Compounds and Radiopharmaceuticals, vol. 22, No. 8, pp. 851–862.
Chemical Abstracts, vol. 68, No. 23, p. 10099, Abstract #104713e, Jun. 3, 1968.
Martinez et al., J. Med. Chem., 1982, vol. 25, pp. 178–182.
Ahmad et al., Canadian Journal of Chemistry, vol. 45, 1967, pp. 1539–1542.
Daum et al., Chemical Abstracts, vol. 72, No. 9, p. 408, 43235j (1960).

Primary Examiner—Donald B. Moyer
Assistant Examiner—Julie K. Parker
Attorney, Agent, or Firm—Foley & Lardner, Schwartz, Jeffery, Schwaab, Mack, Blumenthal & Evans

[57] ABSTRACT

The subject of the invention is a novel procedure for the preparation of the compounds of formula I:

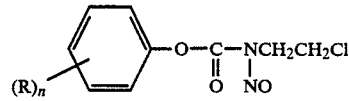

in which n varies in particular from 2 to 5 and R represents Cl, Br or F

Z represents in particular hydrogen, characterized in that the halogenoformate of formula II:

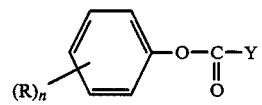

R and n having the meanings indicated above, Y representing a halogen, is made to react with $NH_2CH_2CH_2Cl$ to form the compound of formula Ia:

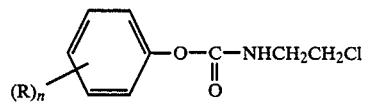

in which R has the meanings indicated above, and in that the compound Ia is treated directly with nitrosylsulfuric acid.

5 Claims, 2 Drawing Sheets

SPECTRE RMN (100MHz)

PROCEDURE FOR THE PREPARATION OF ACTIVATED NITROSOCARBAMATES

The subject of the invention is a novel procedure for the preparation of activated nitrosocarbamates which makes it possible to avoid the use of isocyanates, on the one hand, and enables the nitrosation to be performed under advantageous conditions, on the other, in particular in regard to yield and the purity of the nitrosocarbamates obtained.

The procedure of the invention can be applied with advantage to the preparation of nitrosoureas in particular, without recourse being necessary to the use of an isocyanate.

Hitherto, isocyanates have been used for the preparation of nitrosoureas and, for this purpose, are made to react with a primary or secondary amine leading to the generation of the

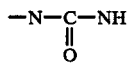

function, which may be subsequently nitrosated by means of an alkali metal nitrite such as sodium nitrite, for example.

Isocyanates are also used for the preparation of nitrosoureas in a reaction scheme which consists of reacting an isocyanate such as methyl isocyanate, 2-chloroethyl isocyanate or cyclohexylisocyanate with an activated phenol such as 2,4,5-trichlorophenol, pentachlorophenol or pentafluorophenol (cf. French patent No. 80 16453, J. Med. Chem. vol 25, No. 2, 1982, 178–182) leading to the formation of ureas which are then converted into nitrosoureas by means of nitrosyl chloride.

But, isocyanates are relatively toxic substances which, as a consequence of certain regulations, must be manufactured on the premises and used in situ.

In order to avoid the use of isocyanates in the preparation of nitrosourea derivatives, the use of $^{14}C$ N-(2-chloroethyl) paranitrophenyl carbamate has been suggested (cf. Madelmont et al, Journal of Labelled Compounds and Radiopharmaceuticals—vol. XXII No. 8, p. 851–862), obtained by reaction of paranitrophenyl chloroformate with $^{14}C$ 2-chloroethylamine, nitrosation being then carried out by nitrosyl chloride in order to prepare a labelled compound. However, the use of N-(2-chloroethyl) paranitrophenyl carbamate possesses the disadvantage of giving rise to only certain nitrosoureas and under reaction conditions which make the separation of the reaction products difficult (cf. French patent No. 2 487 343).

The preparation of N-alkyl carbamates by reacting a halogenoformate with a primary amine has also been described. In the French patent No. 2089433, halogenoformate bearing a fluoromethyl group was made to react with amines of the formula HNRR'; in the summary of Chem. Abstract 68 No. 23, June 3, 1968, p. 10099, a 2,4,6-trichlorophenyl ester of chlorocarbonic acid is treated with an alkylamine or a cycloalkylamine; in patent No. 1020971, a halogenoformate is treated with a primary amine $RNH_2$ in which R is a phenyl nucleus or a substituted phenyl nucleus.

However, none of these earlier documents describes or suggests the subsequent nitrosation of the carbamates obtained or their use for the preparation of nitrosoureas.

The nitrosation of N-alkyl carbamates by various nitrosation reagents, in particular $N_2O_4$, $N_2O_3$, NOBr, NOCl, alkyl nitrites or acid (hydrochloric or sulfuric) and sodium nitrite has also been described. In this last case, side reactions may occur concomitantly, the yields are not always satisfactory and the product obtained is difficult to purify (French patent No. 73625 and U.S. Pat. No. 3345256). None of these documents describes the direct nitrosation of carbamates by means of nitrosylsulfuric acid.

One of the features of the invention is to suggest a novel procedure for the preparation of nitrosocarbamates which avoids the use of isocyanates.

Another feature of the invention is to suggest a novel procedure for the preparation of nitrosoureas which avoids the use of isocyanates on the one hand, and, on the other, enables the nitrosation to be performed under advantageous conditions.

These different features of the invention are obtained by implementing a procedure which is composed of the combination of the following two steps: the first step csnsists of reacting a primary amine with a halogenoformate, in particular a chloroformate, instead of the isocyanate normally used in order to form an activated carbamate and the second step consists of reacting nitrosylsulfuric acid directly with the activated carbamate obtained in the first step in order to nitrosate the said activated carbamate and produce a nitrosocarbamate.

The procedure according to the invention for the preparation of the compounds of formula I:

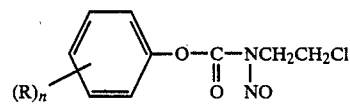

in which n varies from 2 to 5 and R represents Cl, Br or F is characterised in that, in the first step, a halogenoformate of formula II:

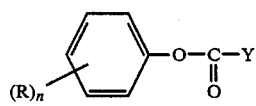

in which R and n have the meanings indicated above and Y represents a halogen, in particular chlorine, is made to react with the amine $NH_2CH_2CH_2Cl$, in order to produce the compound of formula Ia:

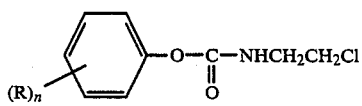

in which R has the meanings indicated above and in that, in the second step, the compound Ia mentioned above is treated directly with nitrosylsulfuric acid.

According to another preferred embodiment of the procedure of the invention, the halogenoformate used is a chloroformate of the following formula IIa:

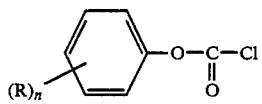

in which R and n have the meanings indicated above.

According to another advantageous embodiment of the procedure of the invention, pentachlorophenyl chloroformate or pentafluorophenyl chloroformate is used as chloroformate.

According to another embodiment of the procedure of the invention, the halogenoformate used has the formula:

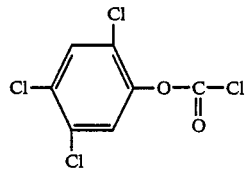

which leads, in the first step after condensation of this halogenoformate with $NH_2CH_2CH_2Cl$, to the compound of formula IV

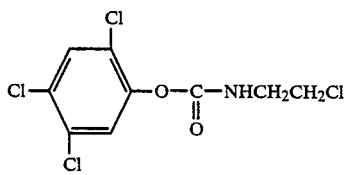

which, in the second step, is treated directly with nitrosylsulfuric acid to give the compound of formula V:

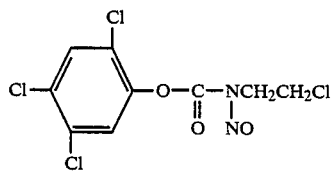

Of the halogenoformates, in particular the chloroformates used in the procedure of the invention, 2,4,5-trichlorophenylchloroformate is commercially available or can be synthesised according to the procedure described in Broadbent W. J. Chem. Soc. C, 1967, t. 24, pp. 2632–2636.

The chloroformates are obtained by reacting the phenol bearing the appropriate substituents with phosgene.

The procedure of the invention leads to the preparation of nitrosocarbamates which are useful for the preparation of nitrosoureas by direct condensation of a nitrosocarbamate with the amine group of the sugar of which one wishes to form the corresponding nitrosourea.

The invention will be better understood by consulting the examples below which serve to illustrate the procedure of the invention without implying limitations.

EXAMPLE 1

Preparation of a reagent used in the procedure of the invention: 2,4,5-trichlorophenyl N-(2-chloroethyl)-N-nitrosocarbamate This preparation is carried out in two steps:

(1) Preparation of 2,4,5-trichlorophenyl N-(2-chloroethyl)-carbamate.

The reaction scheme is as follows:

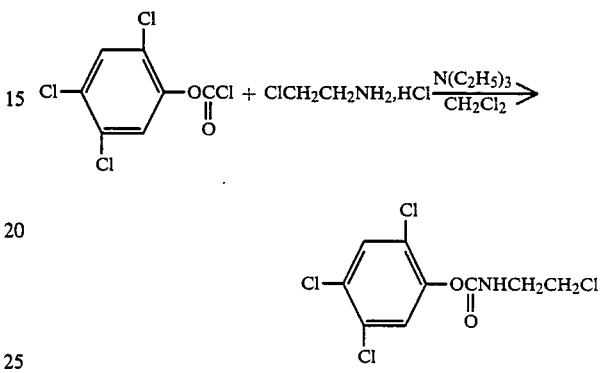

| Reagents | 2,4,5-trichlorophenylchloroformate | 10.4 g |
|---|---|---|
| | 2-chloroethylamine hydrochloride | 4.65 g |
| | redistilled triethylamine | 10 ml |
| | anhydrous methylene chloride | 200 ml |

To a solution of 2,4,5-trichlorophenylchloroformate (10.4 g, 0.04 mole) in anhydrous methylene chloride (100 ml) is added dropwise with stirring at 0° C. a solution of 2-chloroethylamine hydrochloride (4.65 g, 0.04 mole) and triethylamine (10 ml) in 100 ml of anhydrous methylene chloride.

After being stirred for 18 hours at ambient temperature, the reaction mixture is washed several times with a minimum of water until chloride ion can no longer be detected, the resulting organic phase is dried over sodium sulfate and then evaporated to dryness in a vacuum.

The 2,4,5-trichlorophenyl N-(2-chloroethyl)-carbamate (11.1 g, 91%) is isolated in the form of greyish-white crystals.

m.p.: 106°–107° C.

TLC: petroleum ether (40°–65° C.)—ethyl ether (2:1 v/v); revelation by iodine.

R.f.: 0.4.

IR (KBr): 3350 cm$^{-1}$ (NH), 1720 cm$^{-1}$ (carbonyl).

NMR spectrum (chloroform-d): 3.54–3.73 (m, $CH_2CH_2Cl$), 5.68 (s, NH), 7.36 and 7.53 (H aromatics).

The purity of the 2,4,5-trichlorophenylchloroformate must be checked before it is used (m.p.>60° C., litt. m.p.: 65° TLC hexane-ethyl ether (2:1, v/v), revelation: single spot in UV, Rf=0.5).

In certain cases it is necessary to recrystallise the commercial product from hexane in order to obtain the analytical data specified above.

The NMR spectrum of the 2,4,5-trichlorophenyl N-(2-chloroethyl)-carbamate (100 MHz) is shown in FIG. 1.

(2) Preparation of 2,4,5-trichlorophenyl N-(2-chloroethyl)-N-nitroso-carbamate.

The reaction scheme is as follows:

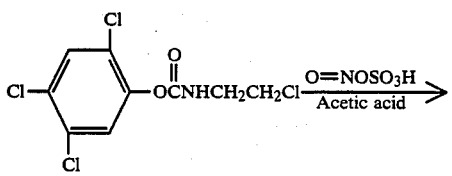

| Reagents: | 2,4,5-trichlorophenyl N—(2-chloroethyl)-carbamate | 12 g |
|---|---|---|
| | nitrosylsulfuric acid | 12.5 g |
| | glacial acetic acid | 100 ml |

To a solution of 2,4,5-trichlorophenyl N-(2-chloroethyl)-carbamate (12 g, 0.04 mole) in glacial acetic acid, nitrosylsulfuric acid (12.5 g, 0.1 mole) is added portionwise in the cold.

After being stirred at 25° C. for 4 hours, the reaction mixture is poured into water (1 600 ml), then extracted with ethyl ether; the organic phase is washed with water until it becomes neutral, dried over sodium sulfate and filtered. The residue obtained upon evaporation is taken up in petroleum ether (40° C.). After 18 h at 0° C. the crystals are filtered off to give 11 (10.5 g, 80%). M.p.: 62° C.

TLC: petroleum ether (40°–65° C.)—ethyl ether (2:1, v/v): revelation: Griess reaction. R.f.: 0.8.

IR (KBr): 1770 cm$^{-1}$ (carbonyl), 1500 and 1480 cm$^{-1}$ (nitroso).

NMR spectrum (chloroform-d): 3.56 (t, CH$_2$—N, J=J'=6 Hz), 4.19 (t, CH$_2$—Cl, J=J'=6 Hz), 7.54 and 7.64 (s, H aromatics).

Figure 2:
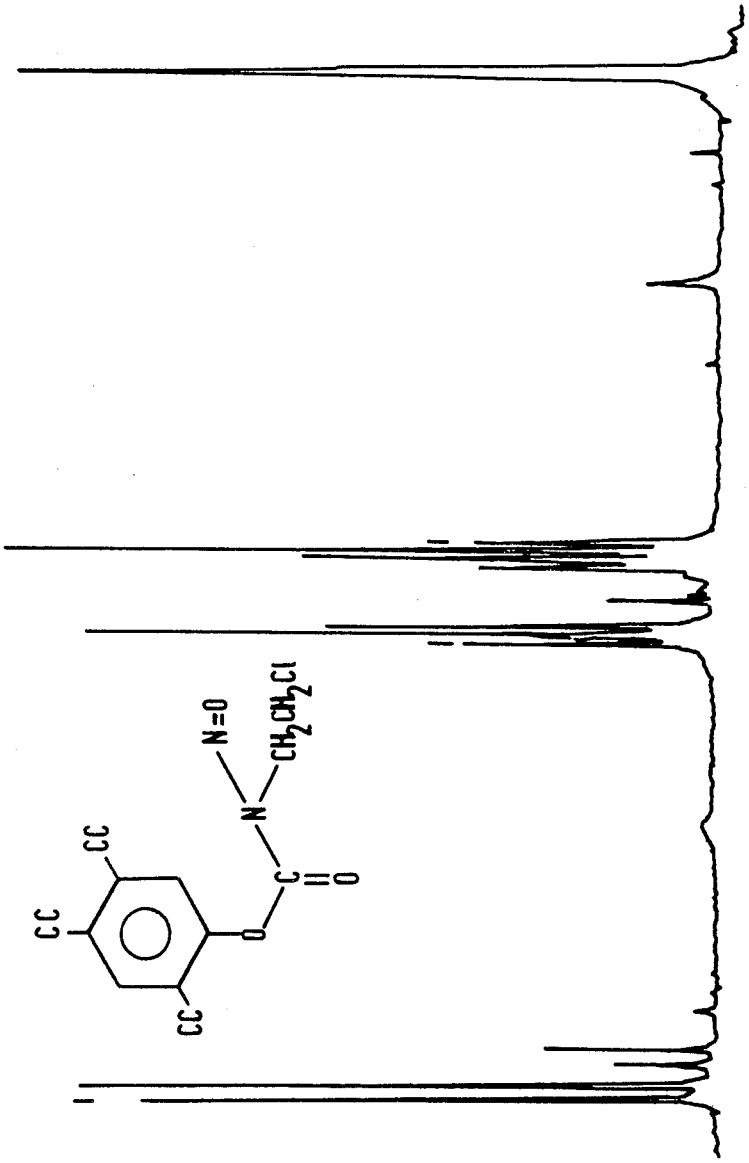

The NMR spectrum of 2,4,5-trichlorophenyl N-(2-chloroethyl)-carbamate (100 MHz) is shown in FIG. 2.

EXAMPLE 2

Preparation of methyl 3-[3-(2-chloroethyl) 3-nitroso ureido]2,3,6-trideoxy-β-L-arabino-hexopyranoside (IC 1615).

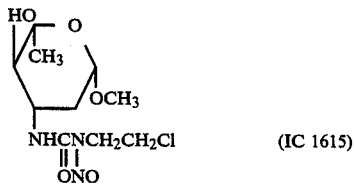

(a) Preparation of methyl 3-azido 2,3,6-trideoxy-β-L-arabino-hexopyranoside 3 g (0.016 mole) of methyl 3-azido 2,3,6-trideoxy-α-L-arabino-hexopyranoside and 1 g of tosic acid in 50 ml of anhydrous methanol are stirred for 48 hours at ambient temperature.

The reaction mixture is evaporated to dryness in a vacuum. The residue is taken up in methylene chloride. After being washed twice with water, the organic phase is dried over sodium sulfate, evaporated to dryness in a vacuum and chromatographed on a column of silica (eluant: hexane-ethyl acetate, 5:1).

Analysis: C$_7$H$_{13}$N$_3$O$_3$=187.20. M.P.: 72°–73° (hexane). [α]$_D$=+63.5° (c, 0.8 CHCl$_3$). IR (Nujol) 3370 cm$^{-1}$ (azide).

(b) Preparation of methyl 3-amino 2,3,6-trideoxy-β-L-arabino-hexopyranoside

This compound is prepared by dissolving 5 g of methyl 3-azido 2,3,6-trideoxy-β-L-arabino-hexopyranoside in 10 ml of methanol and by stirring the solution for 12 hours in an atmosphere of hydrogen in the presence of triethylamine (1 ml) and 10% palladium on charcoal (1 g). The catalyst is removed by filtration.

Analysis: C$_7$H$_{15}$NO$_3$=161.20. Yield=85%. M.P.: 136°. [α]$_D$: +75.8° (c, 0.5, CHCl$_3$).

(c) Preparation of methyl 3-[3-(2-chloroethyl) 3-nitroso ureido]2,3,6-trideoxy-β-L-arabino-hexopyranoside Methyl 3-amino 2,3,6-trideoxy-β-L-arabino-hexopyranoside is dissolved in DMF, then 2,4,5-trichlorophenyl N-(2-chloroethyl)-N-nitroso-carbamate is added according to the procedure of the invention.

After being stirred at 0° C. for 4 hours the reaction mixture is evaporated. The compound obtained (IC 1615) is a new compound and it has the following properties:

Analysis: C$_{10}$H$_{18}$ClN$_3$O$_5$=295.7. M.P.: 109°–110°. [α]$_D$: +22.8° (c, 0.5% CHCl$_3$).

EXAMPLE 3

Preparation of methyl 3-[3-(2-chloroethyl) 3-nitroso ureido]2,3,6-trideoxy-β-D-arabino-hexopyranoside (IC 1625)

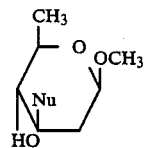

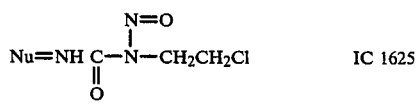

This compound is obtained from methyl 3-amino 2,3,6-trideoxy-β-D-arabino-hexopyranoside by using 2,4,5-trichlorophenyl N-(2-chloroethyl)-N-nitroso-carbamate according to the procedure of the invention as described in relation to the preparation of compound IC 1615.

The compound IC 1625 obtained is new.

The properties of the compound obtained are as follows:

Analysis: C$_{10}$H$_{18}$ClN$_3$O$_5$=295.7. M.P.: 103–105. $_D$=−25.0 (c=0.3% CHCl$_3$).

EXAMPLE 4

Preparation of methyl 3-[3-(2-chloroethyl) 3-nitroso ureido]2,3-dideoxy-β-D-arabino-hexopyranoside (IC 1673)

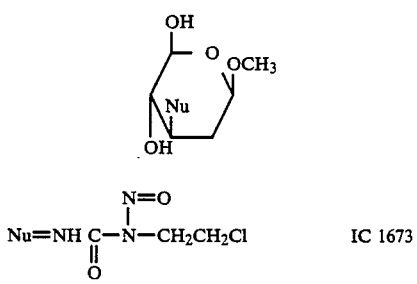

(a) Preparation of methyl 3-azido 2,3-dideoxy-β-D-arabino-hexopyranoside 19.2 g (0.095 mole) of methyl 3-azido 2,3-dideoxy-α-D-hexopyranoside prepared according to the European patent application No. 84 401743 and 1 g of tosic acid in 200 ml of methanol are stirred for 48 hours at ambient temperature. The residue obtained after evaporation in a vacuum is taken up in 60 ml of anhydrous pyridine.

The temperature is maintained at 15° while 30 g of acetic anhydride are added dropwise. After being stirred for 16 hours, the reaction mixture is evaporated to dryness. The residue is taken up in methylene chloride; the organic phase is washed with a solution of 2NHCl, then with water, and finally with a solution of sodium bicarbonate. The organic phase is dried over sodium sulfate, evaporated in a vacuum and gives, after chromatography on silica (eluant: hexane 4 acetone 1), 19.5 g of compound 3 in the form of the diacetate and 2.5 g of methyl 3-azido 2,3-dideoxy-β-D-arabino-hexopyranoside in the form of the diacetate.

This latter compound is taken up in 45 ml of anhydrous methanol, and then 5 ml of sodium methylate are added. After being stirred for 4 hours, the solution is neutralised by the addition of Amberlite IRC50 resin. After evaporation, the filtrate gives methyl 3-azido 2,3-dideoxy-β-D-arabino-hexopyranoside in the form of crystals.

Analysis: $C_7H_{13}N_3O_4$: 203.2.

(b) Preparation of methyl 3-amino 2,3-dideoxy-β-D-arabino-hexopyranoside

This compound is prepared by dissolving 5 g of methyl 3-azido 2,3-dideoxy-β-D-arabino-hexopyranoside in 10 ml of methanol and by stirring the solution for 12 hours in an atmosphere of hydrogen in the presence of triethylamine (1 ml) and 10% palladium on charcoal (1 g). The catalyst is removed by filtration.

Analysis: $C_7H_{15}NO_4$: 177. M.P.: 140–142. $[\alpha]_D$: −61.8 (c 0.55% MeOH).

(c) Preparation of methyl 3-[3-(2-chloroethyl) 3-nitroso ureido]2,3-dideoxy-β-D-arabino-hexopyranoside Methyl 3-amino 2,3-dideoxy-β-D-arabino-hexopyranoside is dissolved in DMF (dimethyl formamide), then 2,4,5-trichlorophenyl N-(2-chloroethyl)-N-nitroso-carbamate is added according to the procedure of the invention.

After being stirred at 0° C. for 4 hours, the reaction mixture is evaporated. The compound obtained (IC 85-1673) is a new compound and has the following properties:

Analysis: $C_{10}H_{18}ClN_3O_6$: 311.72. Yield: 70%. M.P.: 68°–70°. $[\alpha]_D$: −37.9 (c, 0.36% MeOH).

EXAMPLE 5

Preparation of methyl 3-3-(2-chloroethyl) 3-nitroso ureido 3,4,6-trideoxy-α-L-xylo-hexopyranoside (IC 1626)

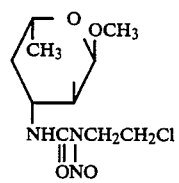

This compound is obtained from methyl 3-amino 3,4,6-trideoxy-α-L-xylo-hexopyranoside prepared according to H. Baer, Canad. J. Chem., vol. 52, 1974, p. 122–124, which is dissolved in DMF, and then 2,4,5-trichlorophenyl N-(2-chloroethyl)-N-nitroso-carbamate is added according to the procedure of the invention.

After being stirred at 0° C. for 4 hours the reaction mixture is evaporated. The compound obtained (IC 1626) is a new product and its properties are as follows:

Analysis: $C_{10}H_{18}ClN_3O_5$: 295.7. Yield: 65%. M.P..: 103°–105°. $[\alpha]_D$: = −141.5° (c, 0.71 CHCl$_3$).

EXAMPLE 6

Preparation of methyl 3-[3-(2-chloroethyl) 3-nitroso ureido]3,4,6-trideoxy-β-L-xylo-hexopyranoside (IC 1627).

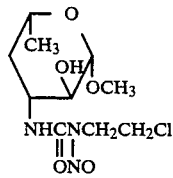

(a) Preparation of methyl 3-nitro 3,4,6-trideoxy-β-L-xylo-hexopyranoside

To 1.8 g of the α anomer above, 40 ml of N methanolic hydrogen chloride are added. After being refluxed for 2 hours, the reaction mixture is evaporated to dryness, then purified on a column of silica (eluant CH$_2$Cl$_2$—MeOH 98:2).

500 mg of the pure β anomer are obtained.

(b) Preparation of methyl 3-amino 3,4,6-trideoxy-β-L-xylo-hexopyranoside

The preceding compound is hyrogenated at atmospheric pressure in the presence of platinum oxide in ethanol.

Analysis: $C_7H_{15}NO_3$: 161. Yield: 80%. M.P.: 146°–148°. $[\alpha]_D$: = +36.0° (c, 0.96 CHCl$_3$).

(c) Preparation of methyl 3-[3-(2-chloroethyl) 3-nitroso ureido]3,4,6-trideoxy-β-L-xylo-hexopyranoside The methyl 3-amino 3,4,6-trideoxy-β-L-xylo-hexopyranoside is dissolved in DMF, and then 2,4,5-trichlorophenyl N-(2-chloroethyl)-N-nitrosocarbamate is added according to the procedure of the invention.

After being stirred at 0° C. for 4 hours, the reaction mixture is evaporated. The compound obtained (IC 1627) is a new compound and its properties are as follows:

Analysis: $C_{10}H_8ClN_3O_5$: 295.7. M.P.: 90°–92° (isopropyl ether). $[\alpha]_D$: −9.0° (c, 0.6 CHCl$_3$).

EXAMPLE 7

Preparation of methyl 3-[3-(2-chloroethyl)-3-nitroso ureido]3,4,6-trideoxy-α-D-xylo-hexopyranoside (IC 1590)

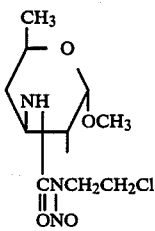

(a) Preparation of methyl 2-O-acetyl 3-azido 4,6-dichloro 3,4,6-trideoxy-α-D-galacto-hexopyranoside To 44 g (0.21 mole) of 3-azido 3-deoxy-D-glucopyranose in 160 ml of anhydrous pyridine and 200 ml of chloroform cooled to −78° C., 52 ml of sulfuryl chloride are added dropwise. After 2 hours at −78° C., the mixture is stirred for 5 hours at ambient temperature.

The reaction mixture is diluted with 400 ml of chloroform, then washed with 2N hydrochloric acid, water, then with a solution of sodium bicarbonate and again with water. After drying over sodium sulfate and evaporation to dryness in a vacuum, the residue obtained is taken up in 200 ml of methanol and then a 10% solution of potassium iodide in a water-methanol mixture (1:1) is added.

The solution is neutralised by potassium bicarbonate, filtered, evaporated and then the residue is taken up in chloroform. The organic phase is washed with a sodium thiosulfate solution followed by water, dried over sodium sulfate and evaporated.

The residue is taken up in 100 ml of pyridine cooled to 0°. 20 ml of acetic anhydride are added dropwise, the reaction mixture is stirred for 1 day and then evaporated in a vacuum, the aqueous phase is extracted 2 or 3 three times with 200 ml of methylene chloride. The organic phase is then washed with water, evaporated to dryness in a vacuum and 36 g of a mixture corresponding to the two anomers, α and β are obtained.

The 2 anomers are isolated in the pure state by chromatography on a column of silica (eluant: hexane-acetone 10:1).

α anomer 14.5 g, m.p.: 74°–76° (hexane-ethyl acetate). $[\alpha]_D$=+171° (c, 1.17 CHCl$_3$).

β anomer 16.0 g, m.p.: 108°–110° (hexane-ethyl acetate). $[\alpha]_D$=−6.5° (c, 1.58 CHCl$_3$).

(b) Preparation of methyl 3-azido 4,6-dichloro 3,4,6-trideoxy-α-D-galacto-hexopyranoside 5 g (0.017 mole) of the preceding anomer are dissolved in 50 ml of anhydrous methanol in the presence of 1 g of tosic acid. The reaction mixture is left to stand for 18 hours at ambient temperature, then is evaporated to dryness in a vacuum. The residue is taken up in methylene chloride, the organic phase is washed twice with water, dried, filtered and then evaporated.

The crystals obtained (4.2 g) are recrystallised from a mixture of hexane-ethyl acetate.

Analysis: $C_7H_{11}Cl_2N_3O_3$: 256. M.P.: 139°–141°. $[\alpha]_D$:=+188° (c, 1.035 CH$_3$OH).

(c) Preparation of methyl 3-amino 3,4,6-trideoxy-α-D-xylo-hexopyranoside

To 2 g (0.0075 mole) of the preceding compound in 50 ml of anhydrous toluene under nitrogen are added 0.5 g of 2,2'-azobisisobutyronitrile followed dropwise by 8 ml of tributyl tin hydride. The reaction mixture is heated at reflux for 10 hours. After being cooled the precipitate is filtered off and the filtrate is evaporated to dryness in a vacuum. After chromatography on silica (eluant CH$_2$Cl$_2$-ammoniacal MeOH, 9:1) the pure amino sugar is obtained in the form of white crystals.

Analysis: $C_7H_{15}NO_3$: 161. M.p.: 136°–139° (ether-methanol). $[\alpha]_D$: +172° (c, 1% CHTCl$_3$).

(d) Preparation of methyl 3-[3-(2-chloroethyl) 3-nitroso ureido]3,4,6-trideoxy-α-D-xylo-hexopyranoside (IC 1591)

Methyl 3-amino 3,4,6-trideoxy-α-D-xylo-hexopyranoside is dissolved in DMF, then 2,4,5-trichlorophenyl N-(2-chloroethyl)-N-nitroso-carbamate is added according to the procedure of the invention.

After being stirred for 4 hours at 0° C., the reaction mixture is evaporated. The compound obtained (IC 1590) is a new compound and its properties are as follows:

Analysis: $C_{10}H_{18}ClN_3O_5$: 295.7. Yield: 65%. M.p.: 103°–105°. $[\alpha]_D$: 138° (c, 1.41 CHCl$_3$).

EXAMPLE 8

Preparation of methyl 3-[3-(2-chloroethyl)3-nitroso ureido]3,4,6-trideoxy-β-D-xylo-hexopyranoside (IC 1591)

(a) Preparation of methyl 2-O-acetyl 3-azido 4,6-dichloro 3,4,6-trideoxy-β-D-galacto-hexopyranoside To 44 g (0.21 mole) of 3-azido 3-deoxy-D-glucopyranose in 160 ml of anhydrous pyridine and 200 ml of chloroform cooled to −78°, 52 ml of sulfuryl chloride are added dropwise. After 2 hours at −78° C., the mixture is stirred for 5 hours at ambient temperature.

The reaction mixture is diluted with 400 ml, then washed with 2N hydrochloric acid, water, then with a solution of sodium bicarbonate and again with water. After drying over sodium sulfate and evaporation to dryness in a vacuum, the residue is taken up in 200 ml of methanol and then a 10% solution of potassium iodide in a water-methanol mixture (1:1) is added.

The solution is neutralised by potassium bicarbonate, filtered, evaporated and the residue is taken up in chloroform. The organic phase is washed with a sodium thiosulfate solution and then with water, dried over sodium sulfate.

The residue is taken up in 100 ml of pyridine cooled to 0°. 20 ml of acetic anhydride are added dropwise at 0°, the reaction mixture is stirred for 1 day and then is evaporated in a vacuum, the aqueous phase is extracted 2 or 3 times with 200 ml of methylene chloride. The organic phase is then washed with water, evaporated to dryness in a vacuum and 36 g of a mixture corresponding to the two anomers, α and β, are obtained.

After chromatography on a column of silica (eluant: hexane-acetone 10:1) the two anomers are isolated in the pure state.

α anomer 14.5 g.
M.p.: 74°-76° (hexane-ethyl acetate).
$[\alpha]_D = +171°$ (c, 1.17 CHCl$_3$).
β anomer 16.0 g.
M.p.: 108°-110° (hexane-ethyl acetate).
$[\alpha]_D$: −6.5° (c, 1.58 CHCl$_3$).

(b) Preparation of methyl 3-azido 4,6-dichloro 3,4,6-trideoxy-β-D-galacto-hexopyranoside The same procedure is used as for part b of IC 1590.
Analysis: $C_7H_{11}Cl_2N_3O_3$: 256. Yield: 85%. M.p.: 135. $[\alpha]_D$: +10.0° (c, 0.97% CH$_3$OH).

(c) Preparation of methyl 3-amino 3,4,6-trideoxy-β-D-xylo-hexopyranoside

The same procedure is used as for part c of IC 1590.
Analysis: $C_7H_{15}NO_3$: 161. M.p.: 148-149. $[\alpha]_D$: −52° (c, 1% CHCl$_3$).

(d) Preparation of methyl 3-[3-(2-chloroethyl) 3-nitroso ureido]3,4,6-trideoxy-β-D-xylo-hexopyranoside Methyl 3-amino 3,4,6-trideoxy-β-D-xylo-hexopyranoside is dissolved in DMF, then 2,4,5-trichlorophenyl N-(2-chloroethyl)-N-nitroso-carbamate is added according to the procedure of the invention.

After being stirred at 0° C. for 4 hours, the reaction mixture is evaporated. The compound obtained (IC 1591) is a new compound and its properties are as follows:

Analysis: $C_{10}H_{18}ClN_3O_5$: 295.7. Yield: 90%. M.p.: 84°-90°. $[\alpha]_D$: +11.5° (c, 1.25 CHCl$_3$).

STUDY OF THE ACTIVITY OF THE COMPOUNDS FROM EXAMPLES 2-8

I—Materials and methods
A—Tumors used
Two murine tumors were used for the "in vivo" studies: the leukemia L1210 and the melanoma B16.
(1) Leukemia L1210
  Animals
    The experiments were always performed on female mice which were specific pathogen-free (S.P.F.) of
    either the line DBA/2JIco
    or line B6 D2 F1/JIco (first generation hybrids between the lines C57BL/6 and DBA/2).
The line used is specified for each series of experiments.
  Tumoral graft
    The day of the graft (by a convention day 0=DO) an inoculum of $1 \times 10^5$ tumor cells in a volume of 0.2 ml is administered to each mouse by the intraperitoneal route (I.P.).
    This inoculum is prepared by diluting ascites fluid taken from the peritoneum of a donor female mouse in NCTC 109 medium (Eurobio Laboratories Paris, France), counting of the cells in a MALASSEZ cell under a microscope and adjustment of the concentration to $5 \times 10^5$ cells per ml.
    The tumor line is an American strain of the line L1210.
  Distribution in experimental groups.

After the tumor has been grafted, the mice are distributed at random in cages of 5 animals. Subsequently, these cages containing 5 mice are themselves distributed at random into a control group (control) and groups treated with the compound IC1625 or IC 1673 defined above in conformity with the procedure of the invention.

(2) Melanoma B16
  Animals
    The experiments were always carried out on SPF female mice B6 D2 F1/JIco (first generation hybrids between the lines C57BL/6 and DBA/2).
  Tumoral graft
    On the day of the graft (day 0) an inoculum of $2 \times 10^6$ tumor cells in a volume of 0.5 ml is administered to each mouse by the intraperitoneal route (I.P.). This inoculum is prepared from a subcutaneous tumor excised from a donor female mouse. After excision, the tumor is fragmented by means of a pair of scissors in the NCTC 109 medium. After filtration through sterile gauze in order to remove large cellular fragments, the homogeneous cell suspension obtained is counted by means of a MALASSEZ cell and diluted to the desired concentration ($4 \times 10^6$ tumor cells per ml) by dilution with the NCTC 109 medium.
  Distribution in experimental groups.
    This was performed in the manner described for the leukemia L1210 (see above).
  b—Protocol for treatment
    The doses of the products IC 1625 and IC 1673 used in the different experiments are expressed in milligrams per kilogram of body weight.
    The products to be injected were dissolved in isotonic sodium chloride solution.
    Two protocols for treatment were used in the different experiments:
      either a single injection on D1 by the intraperitoneal (I.P.) or intravenous (I.V.) route,
      or 3 I.P. injections on D1, D5, D9.
    In each experiment the animals of the control group received 1 or more injections, depending on the experimental protocol used, by the same route (I.P. or I.V.) of the same volume (0.2 ml/20 g) of the vehicle not containing the active principle (isotonic sodium chloride solution).

II—Expression of the results
For each experiment a table specifies:
the number and percentage of the total of the mice surviving to D60,
the T/C for the treated groups.
T representing the mean survival time of the mice in the treated group
C representing the mean survival time of the mice in the control group (control).

III—Comment
The strains of mice used, the experimental protocols and the mode of expression of the results are in accordance with directive 271 F of the "N.C.I. Division of Cancer Treatment" (November 1983).

IV—Pharmacological results

---

IC 1625
L1210 USA - DBA$_2$ - I.P. treatment on D1, D5, D9

-continued

```
                    3 × 10 mg/kg
        T/C         Number of survivors at D60
        190         (0/10)
IC 1673
L1210 USA - B6D2F1 - I.P. treatment on D1, D5, D9
                    3 × 1.25 mg/kg
        T/C         Number of survivors
        158         (0/10)
L1210 USA - B6D2F1 - I.P. treatment on D1, D5, D9
                    3 × 5 mg/kg
        T/C         Number of survivors
        626         (6/10)
Melanoma B16 - B6D2F1 - I.P. treatment on D1, D5, D9
                    3 × 10 mg/kg
        T/C         Number of survivors
        232         (4/10)
IC 1626
L1210 USA - DBA2 - I.P. treatment on D1
                    1 × 20 mg/kg
Number of survivors at D60: 3/10
L1210 USA - DBA2 - I.P. treatment on D1, D5, D9
                    3 × 2.5 mg/kg, 3 × 10 mg/kg
        T/C         Number of survivors at D60
3 × 2.5 150         0/10
3 × 10  275         3/10
IC 1627
L1210 USA - DBA2 - I.P. treatment on D1,
                    1 × 20 mg/kg
Number of survivors at D60: 3/10
L1210 USA - DBA2 - I.P. treatment on D1, D5, D9
                    3 × 2.5 mg/kg, 3 × 10 mg/kg
        T/C         Number of survivors
3 × 2.5 141         0/10
3 × 10  >600        6/10
IC 1591
L1210 USA strain - DBA2 - I.P. treatment on D1
                    1 × 20 mg/kg
        T/C         Number of survivors at D60
        >600        7/10
L1210 USA strain - DBA2 - I.P. treatment on D1, D5, D9
                    3 × 5 mg/kg
        T/C         Number of survivors at D60
        >600        6/10
L1210 USA strain - B6D2F1 - I.P. treatment on D1, D5, D9
                    3 × 1.25 mg, 3 × 5 mg
                    3 × 10 mg/kg
        T/C         Number of survivors at D60
3 × 1.25 116        0/10
3 × 5    217        2/10
3 × 10   >600       8/10
Melanoma B16 - B6D2F1 - I.P. treatment on D1, D5, D9
                    3 × 10 mg/kg
        T/C         Number of survivors at D60
        194         3/10
```

V—Toxicological results

LD0, LD50, single dose given I.P. to mice of the preceding lines.

For the compound IC 1625, the LDO is higher than or equal to 40 mg/kg.

For the compound IC 1673, the LDO is close to 20 mg/kg.

For the compound IC 1590, the LDO is higher than or equal to 25 mg/kg.

For the compound IC 1591, the LDO is higher than or equal to 20 mg/kg.

We claim:

1. Process for preparing a nitrosocarbamate of the formula:

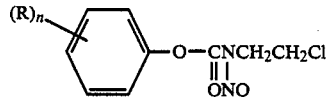

wherein:
n is an integer of 2 to 5; and
R is Cl, Br or F;

comprising the step of reacting nitrosylsulfuric acid with a carbamate of the formula:

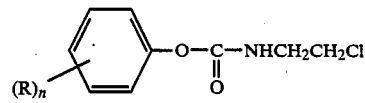

2. The process of claim 1, wherein the carbamate is obtained by reacting $NH_2CH_2CH_2Cl$ with a halogenoformate of the formula:

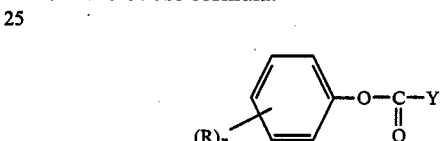

wherein Y is a halogen.

3. The process of claim 2 wherein Y is Cl.

4. The process of claim 2, wherein the halogenoformate is 2,4,5-trichlorophenylchloroformate, pentachlorophenylchloroformate or pentafluorophenylchloroformate.

5. The process of claim 2, wherein the nitrosocarbamate has the formula:

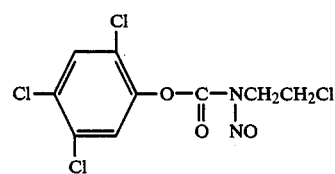

the halogenoformate is 2,4,5-trichlorophenylchloroformate, and the carbamate has the formula:

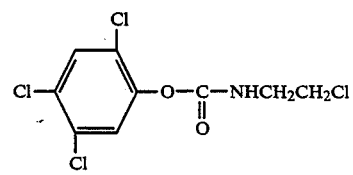

* * * * *